US010821013B2

(12) United States Patent
Dorn et al.

(10) Patent No.: US 10,821,013 B2
(45) Date of Patent: *Nov. 3, 2020

(54) DEVICE TO RELEASE A SELF-EXPANDING IMPLANT

(71) Applicant: C. R. Bard, Inc., Murray Hill, NJ (US)

(72) Inventors: Jurgen Dorn, Neulussheim (DE); Daniel Dietrich, Karlsruhe (DE)

(73) Assignee: C. R. Bard, Inc., Franklin Lakes, NJ (US)

(*) Notice: Subject to any disclaimer, the term of this patent is extended or adjusted under 35 U.S.C. 154(b) by 207 days.

This patent is subject to a terminal disclaimer.

(21) Appl. No.: 16/019,127

(22) Filed: Jun. 26, 2018

(65) Prior Publication Data
US 2018/0333284 A1 Nov. 22, 2018

Related U.S. Application Data

(63) Continuation of application No. 14/923,314, filed on Oct. 26, 2015, now Pat. No. 10,004,624, which is a
(Continued)

(30) Foreign Application Priority Data

Dec. 1, 2010 (GB) .................................. 1020373.5

(51) Int. Cl.
A61F 2/97 (2013.01)
A61F 2/966 (2013.01)

(52) U.S. Cl.
CPC ................ A61F 2/97 (2013.01); A61F 2/966 (2013.01); A61F 2002/9665 (2013.01)

(58) Field of Classification Search
CPC ...... A61M 25/0668; A61M 2025/0675; A61M 2025/1081; A61M 25/005;
(Continued)

(56) References Cited

U.S. PATENT DOCUMENTS 3,953,566 A  4/1976 Gore
3,962,153 A  6/1976 Gore
(Continued)

FOREIGN PATENT DOCUMENTS

DE  10339628 A1  3/2005
EP   0732087 A1  9/1996
(Continued)

OTHER PUBLICATIONS

U.S. Appl. No. 12/958,184, filed Dec. 1, 2010 Advisory Action dated Mar. 30, 2016.
(Continued)

Primary Examiner — George J Ulsh
Assistant Examiner — Andrew P. Restaino
(74) Attorney, Agent, or Firm — Rutan & Tucker LLP

(57) ABSTRACT

A delivery device for a self-expanding implant, including an inner shaft, a slidable member disposed over the inner shaft, an actuation member, a rolling membrane, and a slitting member. The actuation member is coupled to the slidable member, and the rolling membrane is disposed over the self-expanding implant, the rolling member including a proximal end secured to the inner shaft, and a distal end secured to the slidable member. The slitting member includes a proximal end secured to the inner shaft, and a distal end secured to the slidable member, such that translation of the slidable member over the inner shaft in a proximal direction contemporaneously translates the rolling membrane and the slitting member in the proximal direction.

10 Claims, 2 Drawing Sheets

Related U.S. Application Data continuation of application No. 13/309,420, filed on Dec. 1, 2011, now Pat. No. 9,168,164.

(60) Provisional application No. 61/418,657, filed on Dec. 1, 2010.

(58) Field of Classification Search
CPC . A61M 25/0051; A61M 25/0138; A61F 2/95; A61F 2202/9665; A61F 2/2436; A61F 2/962; A61F 2/966; A61F 2/2427; A61F 2002/9665; A61F 2/97
See application file for complete search history.

(56) References Cited

U.S. PATENT DOCUMENTS

| | | |
|---|---|---|
| 4,187,390 A | 2/1980 | Gore |
| 4,636,162 A | 1/1987 | Pavy et al. |
| 4,732,152 A | 3/1988 | Wallsten et al. |
| 5,087,394 A | 2/1992 | Keith |
| 5,217,482 A | 6/1993 | Keith |
| 5,324,261 A | 6/1994 | Amundson et al. |
| 5,453,090 A | 9/1995 | Martinez et al. |
| 5,573,520 A | 11/1996 | Schwartz et al. |
| 5,626,605 A | 5/1997 | Irie et al. |
| 5,647,857 A | 7/1997 | Anderson et al. |
| 5,662,703 A | 9/1997 | Yurek et al. |
| 5,690,644 A | 11/1997 | Yurek et al. |
| 5,709,703 A | 1/1998 | Lukic et al. |
| 5,718,861 A | 2/1998 | Andrews et al. |
| 5,755,769 A | 5/1998 | Richard et al. |
| 5,765,682 A | 6/1998 | Bley et al. |
| 5,776,141 A | 7/1998 | Klein et al. |
| 5,807,520 A | 9/1998 | Wang et al. |
| 5,823,995 A | 10/1998 | Fitzmaurice et al. |
| 5,824,041 A | 10/1998 | Lenker et al. |
| 5,833,694 A | 11/1998 | Poncet |
| 5,843,027 A | 12/1998 | Stone et al. |
| 5,925,061 A | 7/1999 | Ogi et al. |
| 5,968,069 A | 10/1999 | Dusbabek et al. |
| 5,992,000 A | 11/1999 | Humphrey et al. |
| 6,027,510 A | 2/2000 | Alt |
| 6,059,813 A | 5/2000 | Vrba et al. |
| 6,063,092 A | 5/2000 | Shin |
| 6,126,685 A | 10/2000 | Medtronic |
| 6,149,681 A | 11/2000 | Houser et al. |
| 6,168,748 B1 | 1/2001 | Wang et al. |
| 6,224,803 B1 | 5/2001 | Tiernan |
| 6,254,628 B1 | 7/2001 | Wallace et al. |
| 6,309,383 B1 | 10/2001 | Campbell et al. |
| 6,368,344 B1 | 4/2002 | Fitz |
| 6,425,898 B1 | 7/2002 | Wilson et al. |
| 6,447,540 B1 | 9/2002 | Fontaine et al. |
| 6,613,067 B1 | 9/2003 | Johnson |
| 6,613,075 B1 | 9/2003 | Healy et al. |
| 6,629,992 B2 | 10/2003 | Bigus et al. |
| 6,645,238 B2 | 11/2003 | Smith |
| 6,702,843 B1 | 3/2004 | Brown et al. |
| 6,805,703 B2 | 10/2004 | McMorrow |
| 6,833,002 B2 | 12/2004 | Stack et al. |
| 6,837,870 B2 | 1/2005 | Duchamp |
| 6,841,029 B2 | 1/2005 | Lim |
| 6,946,092 B1 | 9/2005 | Bertolino et al. |
| 7,128,956 B2 | 10/2006 | Wang et al. |
| 7,604,668 B2 | 10/2009 | Farnsworth et al. |
| 7,815,669 B2 | 10/2010 | Matsuoka et al. |
| 7,993,350 B2 | 8/2011 | Ventura et al. |
| 8,535,292 B2 | 9/2013 | Tollner et al. |
| 8,568,467 B2 | 10/2013 | Dorn et al. |
| 9,687,369 B2 | 6/2017 | Dorn et al. |
| 9,687,370 B2 | 6/2017 | Dorn |
| 9,724,216 B2 | 8/2017 | Dorn et al. |
| 10,004,624 B2 * | 6/2018 | Dorn ............ A61F 2/966 |
| 10,271,979 B2 | 4/2019 | Dorn et al. |
| 10,278,845 B2 | 5/2019 | Dorn et al. |
| 10,449,072 B2 | 10/2019 | Dorn et al. |
| 10,555,824 B2 | 2/2020 | Dorn et al. |
| 2001/0011180 A1 | 8/2001 | Fitzmaurice et al. |
| 2001/0027323 A1 | 10/2001 | Sullivan et al. |
| 2002/0016597 A1 | 2/2002 | Dwyer et al. |
| 2002/0099431 A1 | 7/2002 | Armstrong et al. |
| 2002/0180107 A1 | 12/2002 | Jackson et al. |
| 2003/0083730 A1 | 5/2003 | Stinson |
| 2003/0093106 A1 | 5/2003 | Brady et al. |
| 2003/0109886 A1 | 6/2003 | Keegan et al. |
| 2003/0114912 A1 | 6/2003 | Sequin et al. |
| 2003/0125709 A1 | 7/2003 | Eidenschink |
| 2003/0125791 A1 | 7/2003 | Sequin et al. |
| 2003/0139801 A1 | 7/2003 | Sirhan et al. |
| 2003/0163193 A1 | 8/2003 | Widenhouse |
| 2003/0204235 A1 | 10/2003 | Edens et al. |
| 2004/0064130 A1 | 4/2004 | Carter |
| 2004/0143272 A1 | 7/2004 | Cully et al. |
| 2004/0143286 A1 | 7/2004 | Johnson et al. |
| 2004/0143315 A1 | 7/2004 | Bruun et al. |
| 2004/0148007 A1 | 7/2004 | Jackson et al. |
| 2004/0199239 A1 | 10/2004 | Austin et al. |
| 2004/0267346 A1 | 12/2004 | Shelso |
| 2005/0004555 A1 | 1/2005 | Pursley |
| 2005/0049667 A1 | 3/2005 | Arbefeuille et al. |
| 2005/0113902 A1 | 5/2005 | Geiser et al. |
| 2005/0240254 A1 | 10/2005 | Austin |
| 2006/0015171 A1 | 1/2006 | Armstrong |
| 2006/0030923 A1 | 2/2006 | Gunderson |
| 2006/0089627 A1 | 4/2006 | Burnett et al. |
| 2006/0100687 A1 | 5/2006 | Fahey et al. |
| 2006/0142838 A1 | 6/2006 | Molaei et al. |
| 2006/0200221 A1 | 9/2006 | Malewicz |
| 2006/0212105 A1 | 9/2006 | Dorn et al. |
| 2006/0247661 A1 | 11/2006 | Richards et al. |
| 2006/0259124 A1 | 11/2006 | Matsuoka et al. |
| 2007/0050017 A1 | 3/2007 | Sims et al. |
| 2007/0055338 A1 | 3/2007 | Dorn |
| 2007/0074805 A1 | 4/2007 | Leeflang et al. |
| 2008/0118546 A1 | 5/2008 | Thatcher et al. |
| 2008/0243224 A1 | 10/2008 | Wallace et al. |
| 2009/0125093 A1 | 5/2009 | Hansen |
| 2009/0204196 A1 | 8/2009 | Weber |
| 2009/0254169 A1 | 10/2009 | Spenser et al. |
| 2009/0312828 A1 | 12/2009 | Vrba |
| 2009/0312831 A1 | 12/2009 | Dorn |
| 2010/0049297 A1 | 2/2010 | Dorn |
| 2010/0168835 A1 | 7/2010 | Dorn |
| 2010/0249907 A1 | 9/2010 | Dorn et al. |
| 2011/0060397 A1 | 3/2011 | Dorn |
| 2011/0118817 A1 | 5/2011 | Gunderson et al. |
| 2011/0137396 A1 | 6/2011 | Dorn et al. |
| 2011/0137400 A1 | 6/2011 | Dorn et al. |
| 2011/0137401 A1 | 6/2011 | Dorn et al. |
| 2011/0137402 A1 | 6/2011 | Dorn et al. |
| 2012/0059448 A1 | 3/2012 | Parker et al. |
| 2012/0083869 A1 | 4/2012 | Wubbeling et al. |
| 2012/0143303 A1 | 6/2012 | Dorn et al. |
| 2017/0296368 A1 | 10/2017 | Dorn et al. |

FOREIGN PATENT DOCUMENTS

| | | |
|---|---|---|
| EP | 0941713 A1 | 9/1999 |
| EP | 1062966 A1 | 12/2000 |
| EP | 0732087 B1 | 6/2003 |
| EP | 1679095 A1 | 7/2006 |
| FR | 2688688 A1 | 9/1993 |
| JP | S59-51863 A | 3/1984 |
| JP | H09-512194 A | 12/1997 |
| JP | 2000-116788 A | 4/2000 |
| JP | 2001-9037 | 1/2001 |
| JP | 2001-299926 A | 10/2001 |
| JP | 2006-515786 A | 6/2006 |
| WO | 8603398 A | 6/1986 |
| WO | 1993017636 A1 | 9/1993 |
| WO | 9415549 A1 | 7/1994 |
| WO | 1995030385 A1 | 11/1995 |
| WO | 9632078 A1 | 10/1996 |
| WO | 1998020812 A1 | 5/1998 |

(56) References Cited

FOREIGN PATENT DOCUMENTS

| | | | |
|---|---|---|---|
| WO | 2000018329 | A1 | 4/2000 |
| WO | 2001008599 | A1 | 2/2001 |
| WO | 2002038084 | A2 | 5/2002 |
| WO | 03002034 | A2 | 1/2003 |
| WO | 2003002019 | A2 | 1/2003 |
| WO | 2004062458 | A2 | 7/2004 |
| WO | 2004066809 | A2 | 8/2004 |
| WO | 2004096091 | A1 | 11/2004 |
| WO | 2005072650 | A1 | 8/2005 |
| WO | 2006019626 | A2 | 2/2006 |
| WO | 2006020028 | A1 | 2/2006 |
| WO | 2006071245 | A1 | 7/2006 |
| WO | 2006086709 | A1 | 8/2006 |
| WO | 2006096229 | A1 | 9/2006 |
| WO | 2006130326 | A2 | 12/2006 |
| WO | 2007103666 | A2 | 9/2007 |
| WO | 2009050265 | A1 | 4/2009 |
| WO | 2009135934 | A1 | 11/2009 |
| WO | 2010076052 | A1 | 7/2010 |
| WO | 2010076057 | A1 | 7/2010 |
| WO | 2010115925 | A1 | 10/2010 |
| WO | 2011067277 | A1 | 6/2011 |
| WO | 2011067280 | A1 | 6/2011 |
| WO | 2012072729 | A1 | 6/2012 |

OTHER PUBLICATIONS

U.S. Appl. No. 12/958,184, filed Dec. 1, 2010 Advisory Action dated May 18, 2015.
U.S. Appl. No. 12/958,184, filed Dec. 1, 2010 Final Office Action dated Feb. 10, 2015.
U.S. Appl. No. 12/958,184, filed Dec. 1, 2010 Final Office Action dated Jan. 4, 2016.
U.S. Appl. No. 12/958,184, filed Dec. 1, 2010 Final Office Action dated Nov. 17, 2016.
U.S. Appl. No. 12/958,184, filed Dec. 1, 2010 Non-Final Office Action dated Aug. 10, 2015.
U.S. Appl. No. 12/958,184, filed Dec. 1, 2010 Non-Final Office Action dated Aug. 5, 2014.
U.S. Appl. No. 12/958,184, filed Dec. 1, 2010 Non-Final Office Action dated Jul. 1, 2016.
U.S. Appl. No. 12/958,184, filed Dec. 1, 2010 Notice of Allowance dated Feb. 22, 2017.
U.S. Appl. No. 15/436,597, filed Feb. 17, 2017 Notice of Allowance dated Apr. 2, 2019.
EP 0815339.7 filed Aug. 21, 2008 Search Report dated Dec. 22, 2008.
EP 12164925.5 filed Jul. 6, 2011 Extended European Search Report dated Jul. 26, 2012.
JP 2011-523429 Office Action dated Jan. 6, 2014.
JP 2011-523429 Office Action dated Jul. 17, 2013.
PCT/EP2008/064036 filed Oct. 17, 2008 International Preliminary Examination Report dated Apr. 20, 2010.
PCT/EP2008/064036 filed Oct. 17, 2008 Search Report dated Jan. 22, 2009.
PCT/EP2008/064036 filed Oct. 17, 2008 Written Opinion dated Jan. 22, 2009.
PCT/EP2009/055592 filed May 8, 2009 International Preliminary Report on Patentability dated Nov. 9, 2010.
PCT/EP2009/055592 filed May 8, 2009 Search Report dated Aug. 3, 2009.
PCT/EP2009/055592 filed May 8, 2009 Written Opinion dated Aug. 3, 2009.
PCT/EP2009/060827 filed Aug. 21, 2009 Preliminary Report on Patentability dated Oct. 19, 2010.
PCT/EP2009/060827 filed Aug. 21, 2009 Search Report dated Nov. 16, 2009.
PCT/EP2009/060827 filed Aug. 21, 2009 Written Opinion dated Nov. 16, 2009.
PCT/EP2009/064057 filed Oct. 26, 2009 International Preliminary Report on Patentability dated Jun. 6, 2011.
PCT/EP2009/064057 filed Oct. 26, 2009 International Search Report dated May 17, 2010.
PCT/EP2009/064057 filed Oct. 26, 2009 Written Opinion dated May 17, 2010.
PCT/EP2010/068620 filed Dec. 1, 2010 International Preliminary Report on Patentability dated Aug. 5, 2011.
PCT/EP2010/068620 filed Dec. 1, 2010 International Search Report dated Apr. 21, 2011.
PCT/EP2010/068620 filed Dec. 1, 2010 Written Opinion dated Apr. 21, 2011.
PCT/EP2010/068627 filed Dec. 1, 2010 International Preliminary Report on Patentability dated Jul. 20, 2011.
PCT/EP2010/068627 filed Dec. 1, 2010 International Search Report dated Apr. 21, 2011.
PCT/EP2010/068627 filed Dec. 1, 2010 Written Opinion dated Apr. 21, 2011.
PCT/EP2011/071489 filed Dec. 1, 2011 International Search Report dated Mar. 6, 2012.
U.S. Appl. No. 12/545,409, filed Aug. 21, 2009 Final Office Action dated Nov. 20, 2013.
U.S. Appl. No. 12/545,409, filed Aug. 21, 2009 Non-Final Office Action dated Apr. 13, 2012.
U.S. Appl. No. 12/545,409, filed Aug. 21, 2009 Non-Final Office Action dated Apr. 29, 2013.
U.S. Appl. No. 12/650,863, filed Dec. 31, 2009 Advisory Action dated Dec. 31, 2012.
U.S. Appl. No. 12/650,863, filed Dec. 31, 2009 Final Office Action dated Oct. 11, 2012.
U.S. Appl. No. 12/650,863, filed Dec. 31, 2009 Non-Final Office Action dated Jun. 8, 2012.
U.S. Appl. No. 12/738,568, filed Apr. 16, 2010 Advisory Action dated Jun. 10, 2011.
U.S. Appl. No. 12/738,568, filed Apr. 16, 2010 Final Office Action dated Mar. 29, 2013.
U.S. Appl. No. 12/738,568, filed Apr. 16, 2010 Non-Final Office Action dated Nov. 2, 2012.
U.S. Appl. No. 12/958,089, filed Dec. 1, 2010 Advisory Action dated Oct. 28, 2011.
U.S. Appl. No. 12/958,089, filed Dec. 1, 2010 Final Office Action dated Aug. 15, 2011.
U.S. Appl. No. 12/958,089, filed Dec. 1, 2010 Non-Final Office Action dated Jun. 20, 2014.
U.S. Appl. No. 12/958,089, filed Dec. 1, 2010 Non-Final Office Action dated Mar. 14, 2013.
U.S. Appl. No. 12/958,123, filed Dec. 1, 2010 Advisory Action dated Oct. 17, 2013.
U.S. Appl. No. 12/958,123, filed Dec. 1, 2010 Final Office Action dated Nov. 19, 2014.
U.S. Appl. No. 12/958,123, filed Dec. 1, 2010 Non-Final Office Action dated Jun. 11, 2014.
U.S. Appl. No. 12/958,123, filed Dec. 1, 2010 Non-Final Office Action dated Mar. 25, 2013.
U.S. Appl. No. 12/958,184, filed Dec. 1, 2010 Advisory Action dated Nov. 5, 2013.
U.S. Appl. No. 12/958,184, filed Dec. 1, 2010 Final Office Action dated Aug. 14, 2013.
U.S. Appl. No. 12/958,184, filed Dec. 1, 2010 Non-Final Office Action dated Mar. 14, 2013.
U.S. Appl. No. 12/958,220, filed Dec. 1, 2010 Advisory Action dated Nov. 5, 2013.
U.S. Appl. No. 12/958,220, filed Dec. 1, 2010 Final Office Action dated Aug. 13, 2013.
U.S. Appl. No. 12/958,220, filed Dec. 1, 2010 Non-Final Office Action dated Mar. 15, 2013.
U.S. Appl. No. 12/991,112, filed Nov. 4, 2010 Advisory Action dated Dec. 23, 2014.
U.S. Appl. No. 12/991,112, filed Nov. 4, 2010 Final Office Action dated May 9, 2013.
U.S. Appl. No. 12/991,112, filed Nov. 4, 2010 Final Office Action dated Sep. 11, 2014.

(56) References Cited

OTHER PUBLICATIONS

U.S. Appl. No. 12/991,112, filed Nov. 4, 2010 Non-Final Office Action dated Apr. 3, 2012.
U.S. Appl. No. 12/958,089, filed Dec. 1, 2010 Advisory Action dated Mar. 30, 2016.
U.S. Appl. No. 12/958,089, filed Dec. 1, 2010 Final Office Action dated Jan. 4, 2016.
U.S. Appl. No. 12/958,089, filed Dec. 1, 2010 Final Office Action dated Nov. 19, 2014.
U.S. Appl. No. 12/958,089, filed Dec. 1, 2010 Non-Final Office Action dated Jul. 2, 2015.
U.S. Appl. No. 12/958,089, filed Dec. 1, 2010 Non-Final Office Action dated Sep. 22, 2016.
U.S. Appl. No. 12/958,089, filed Dec. 1, 2010 Notice of Allowance dated Apr. 4, 2017.
U.S. Appl. No. 15/641,069, filed Jul. 3, 2017 Non-Final Office Action dated Jun. 5, 2019.
U.S. Appl. No. 15/642,246, filed Jul. 5, 2017 Non-Final Office Action dated Aug. 27, 2019.
U.S. Appl. No. 15/642,246, filed Jul. 5, 2017 Non-Final Office Action dated Feb. 5, 2020.
U.S. Appl. No. 12/991,112, filed Nov. 4, 2010 Non-Final Office Action dated Mar. 21, 2014.
U.S. Appl. No. 13/309,420, filed Dec. 1, 2011 Advisory Action dated Feb. 13, 2014.
U.S. Appl. No. 13/309,420, filed Dec. 1, 2011 Final Office Action dated Nov. 8, 2013.
U.S. Appl. No. 13/309,420, filed Dec. 1, 2011 Non-Final Office Action dated Apr. 15, 2013.
U.S. Appl. No. 12/650,863, filed Dec. 31, 2009 Notice of Allowance dated Dec. 31, 2018.
U.S. Appl. No. 12/958,220, filed Dec. 1, 2010 Notice of Allowance dated Jan. 2, 2019.
U.S. Appl. No. 15/436,597, filed Feb. 17, 2017 Non-Final Office Action dated Dec. 31, 2018.

* cited by examiner

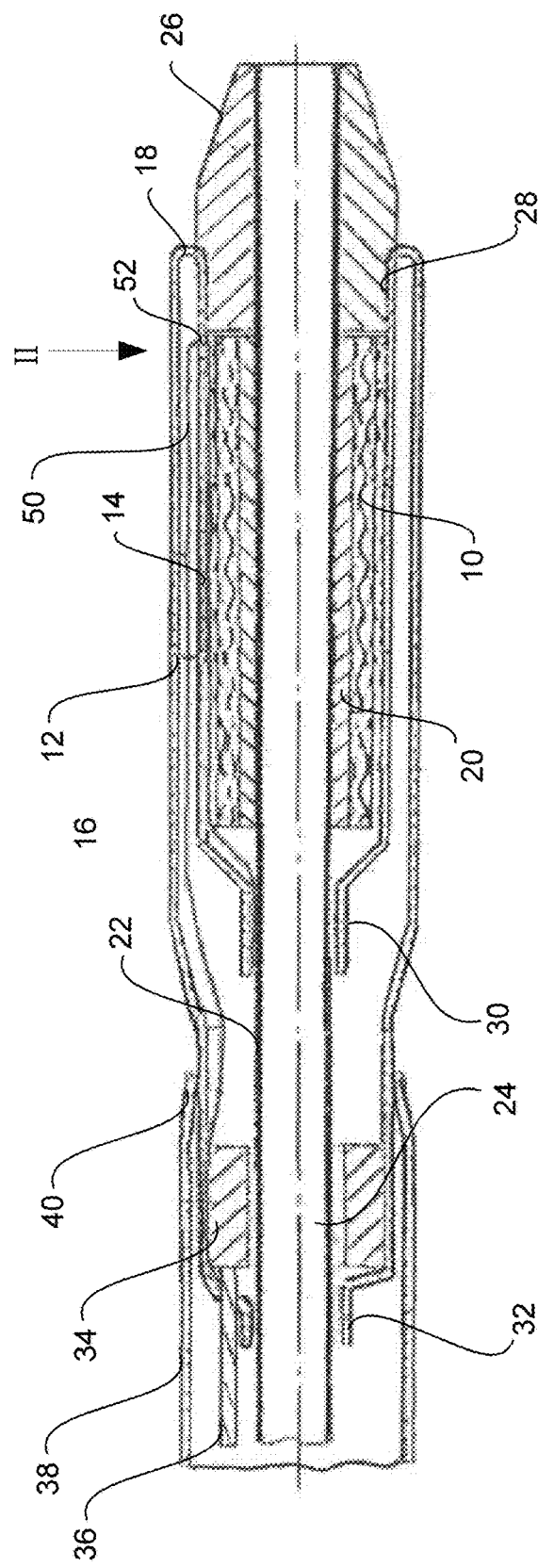
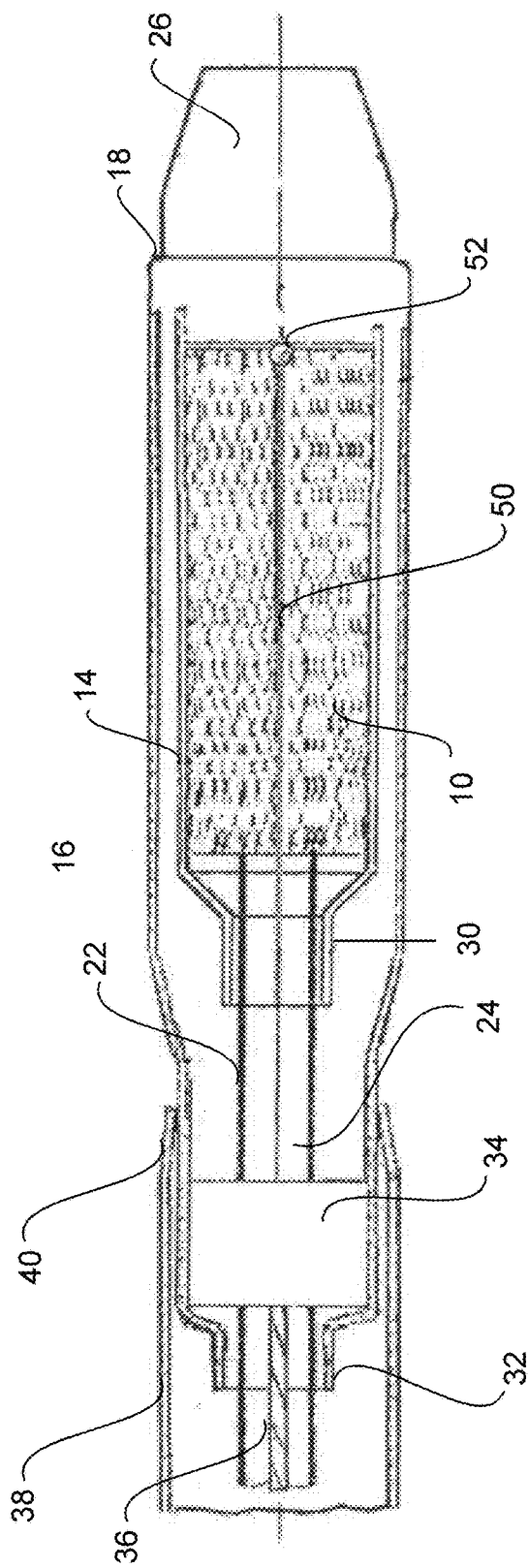
Fig. 1
Fig. 2

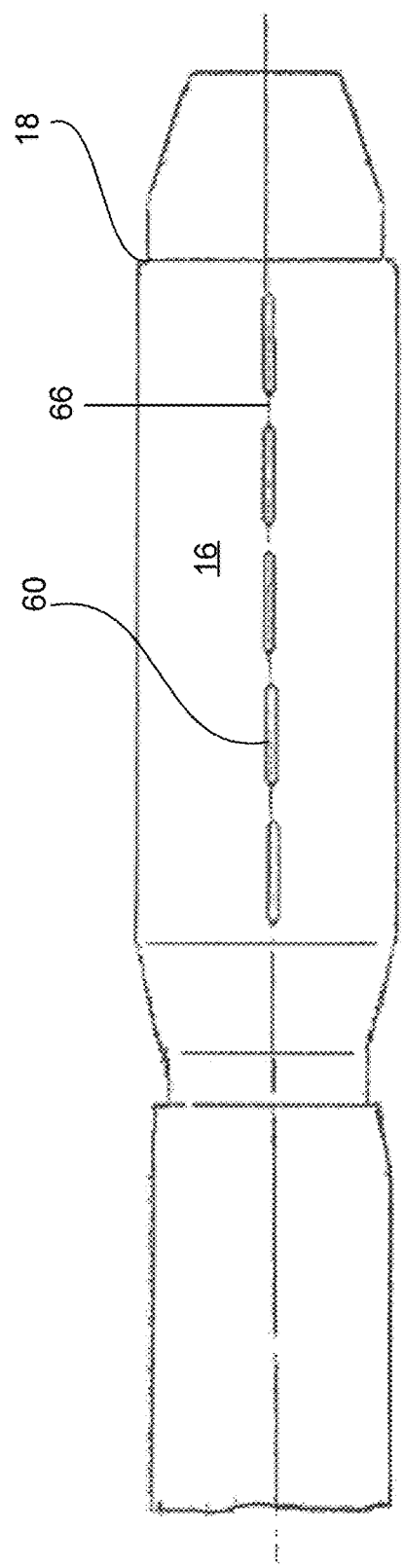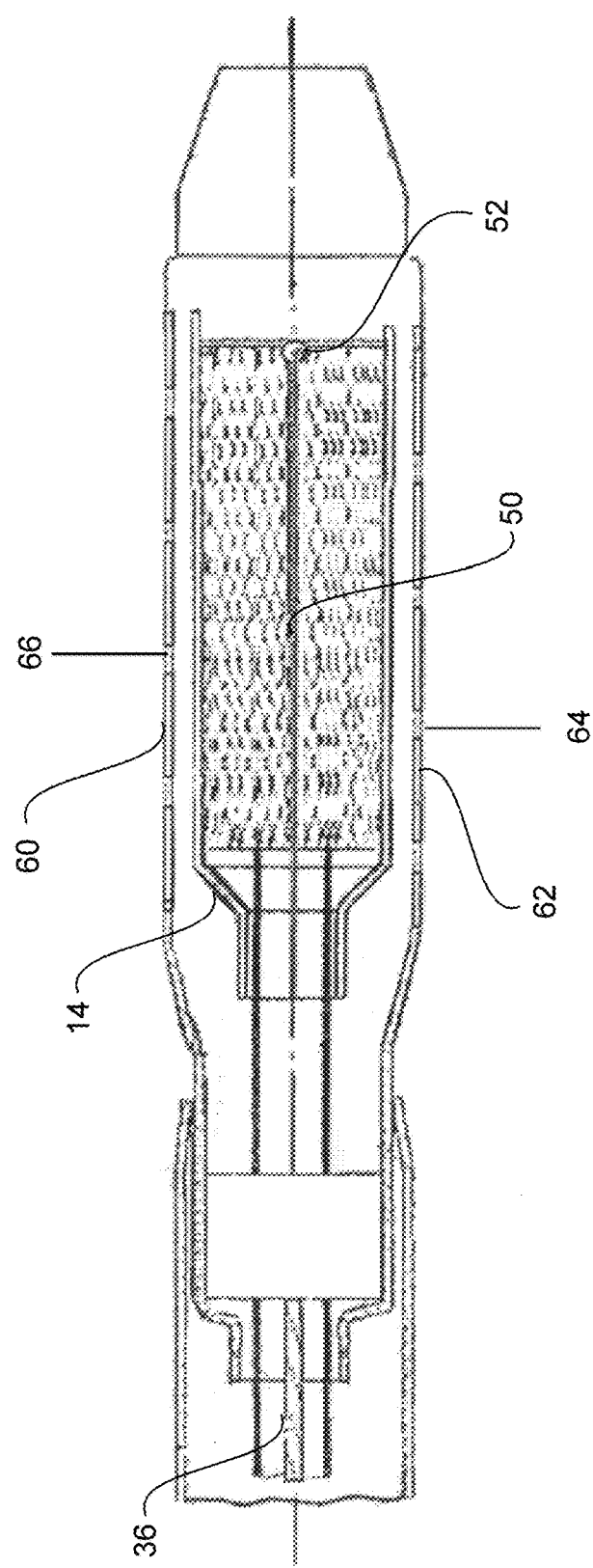

DEVICE TO RELEASE A SELF-EXPANDING IMPLANT

PRIORITY

This application is a continuation of U.S. patent application Ser. No. 14/923,314, filed Oct. 26, 2015, now U.S. Pat. No. 10,004,624, which is a continuation of U.S. patent application Ser. No. 13/309,420, filed Dec. 1, 2011, now U.S. Pat. No. 9,168,164, which claims priority to U.S. Provisional Application No. 61/418,657, filed Dec. 1, 2010, and to United Kingdom Patent Application No. 1020373.5, filed Dec. 1, 2010, each of which is incorporated by reference in its entirety into this application.

TECHNICAL FIELD

This invention relates to a device to release from an implant bed in the device a self-expanding implant by pulling back proximally, the length of the implant, a rolling membrane with an inner sleeve that extends distally to the distal end of the implant bed and an outer sleeve that extends proximally, from the distal end of the inner sleeve, the outer sleeve, during said release, pulling the distal end of the inner sleeve back proximally over the abluminal surface of the remainder of the inner sleeve, proximal of its distal end.

Such devices are disclosed in Applicant's earlier WO 2010/076052 and WO 2010/076057. Other devices that use a rolling membrane are disclosed in, for example, Scimed WO 02/38084 and Gore U.S. Pat. No. 7,198,636. All four documents are incorporated herein by reference in their entirety.

BACKGROUND

Catheter delivery systems for trans-luminal delivery of self-expanding stents have a rich history in the patent literature. Early proposals were for a simple sheath radially surrounding the radially-compressed stent at the distal end of the catheter system, the sheath being pulled back proximally, to release the stent from its bed, progressively, starting at its distal end of the bed, within the stenting site or stenosis of the bodily lumen in which the catheter delivery system had been advanced. Readers will appreciate that, because the stent is self-expanding, it is pressing on the luminal surface of the surrounding sheath, up to the moment of its release from the sheath. Thus, friction forces between the stent and the surrounding sheath must be taken into account when devising a delivery system that will allow the sheath to slide proximally over the full length of the outwardly-pushing, self-expanding stent.

The problems of friction will increase with the length of the stent, and the pressure on delivery system designers is to deliver ever-longer stents. Furthermore, there is steady pressure on stent delivery system designers to come up with systems that have ever-smaller passing diameters at the distal end of the catheter. The conventional unit of dimensions for diameters of systems to advance along a bodily lumen is the "French" which is one third of a millimeter. Thus, one millimeter is "3 French". To be able to reduce the passing diameter of a delivery system, for example from 7 French to 6 French, is a notable achievement.

One way to respond to the challenge of friction forces between a proximally withdrawing sheath and a self-expanding stent confined within it is to adopt a "rolling membrane" sheath system, in which the sheath is at least double the length of the stent that it surrounds, being doubled back on itself at a point distally beyond the distal end of the stent. Then, proximal withdrawal of the radially outer doubled back portion of the sheath length will cause the "rolling edge" between the outer and inner sheath portions to retreat proximally, rolling proximally down the length of the stent, to release the stent progressively, as with a single layer surrounding sheath.

While the rolling membrane approach might solve the problem of friction forces between the proximally retreating sheath and the stent radially inside it, it replaces that problem with another friction issue, namely the need for sliding of the cylinder of the outer sleeve of the sheath over the abluminal surface of the remaining inner sleeve of the sheath that continues to radially constrain the stent within it. It has been proposed to provide a lubricant between the inner and outer radial portions of a rolling membrane release system, but designers would prefer, if possible, to keep to a minimum the use of any extraneous powder or fluid, including lubricants, at the distal end of a catheter. Further, there is the practical difficulty of incorporating into a manufacturing system a step of distributing lubricant as required, consistently and reliably and economically.

Consistency is important, because of the importance of certainty that, when the medical practitioner takes the decision to deploy the self-expanding implant at the distal end of such a catheter delivery system, the components of the delivery system will form as anticipated, every time, to release the implant smoothly and reliably, in the same manner every time. Any sort of unpredictable friction force is anathema to this objective. Hence, designers of these delivery systems will make every effort to minimize the unpredictable effects of friction on the release performance of their system. This is a tough challenge, particularly with the ever-present pressure to accommodate longer stent lengths and smaller passing diameters.

SUMMARY OF THE INVENTION

It is the proposal of the present invention, expressed broadly, to provide in a rolling membrane implant delivery catheter, a slitter. This slitter is caused to move, during release of the implant, proximally along with the outer sleeve of the rolling membrane, thereby to slit longitudinally and progressively the inner sleeve to facilitate its proximal withdrawal, sliding over the abluminal surface of the remaining length of the unslit inner sleeve.

When delivering self-expanding implants, it is of crucial importance to ensure that the system will not release the implant prematurely. With self-expanding stents of ever-greater radial force, confined within a rolling membrane of ever-smaller wall thickness, there is an increasing potential for rupture of the membrane and premature release of the implant, so the rolling membrane sleeve system must be carefully designed to frustrate that possibility. In the present invention, the slitter is arranged to slit the inner sleeve along a line that progresses proximally, but that line starts from a point proximal of the point at the distal end of the sleeve that will constitute the rolling edge of the sleeve during stent release. The start point is located at or near the distal end of the bed in which the self-expanding implant is housed within the delivery system. In this way, it is arranged that the slitter does not commence its slitting action until after an initial proximal movement of the actuator that is used to release the implant from the bed. Up until that point, just distal of the slitter, the circumferential integrity of the inner sleeve can be relied upon to restrain the implant and prevent its outward pressure on the inner sleeve from initiating splitting of the inner sleeve, prior to intended release of the implant, at the location of the splitter. Once the implant release actuator has been actuated, however, the rolling edge of the rolling membrane starts to move proximally, and the slitter starts to slit the inner sleeve. From then on, the process of deployment of the self-expanding implant features a progressive rolling back of the rolling membrane and splitting of the inner sleeve so that, as the implant progressively expands into its deployed disposition in the bodily lumen, the material of the rolling membrane is progressively pulled proximally back from the annulus between the implant and the wall of the bodily lumen so that, once the full length of the implant has been released into the lumen, there is no portion of the rolling membrane remaining within the annulus between the expanded stent and the stented lumen. After that, the catheter delivery system can be withdrawn from the bodily lumen, carrying with it the split material of the rolling membrane.

It is preferred to use as the material of the rolling membrane a cold-drawn polyethylene terephthalate material. For teaching of the use of such material, reference is made to the earlier WO disclosures of the present application, noted above. There is in fact a happy conjunction of material properties, between the cold-drawn PET material and the technical features of the present invention, for the anisotropic molecular lattice of the drawn material facilitates the operation of the slitter.

It is preferred that the inner and outer sleeves of the rolling membrane be contiguous and of the same material. However, it is also contemplated to use different materials, joined at the distal ends of the respective inner and outer sleeves. This would enable the inner sleeve material to be tailored to the functions of the inner sleeve and the outer sleeve material to be tailored to the functions of the outer sleeve.

Thinking again about friction forces, in a system without the slitter, one can imagine that any sort of impediment to the proximal movement of the outer sleeve will result in greater levels of longitudinal stress in the outer sleeve of the rolling membrane proximal of the impediment. Such stresses will have a tendency to reduce the diameter of the outer sleeve under tension. Any such "necking in" of the outer sleeve will, self-evidently, increase forces of friction between the luminal surface of the outer sleeve, sliding over the abluminal surface of the inner sleeve. One can readily imagine that, if the situation worsens, then the system can "bind up", preventing any further proximal movement of the rolling edge and frustrating the ability of the doctor to release the implant any further, possibly resulting in breakage of any component of the catheter delivery system that is in tension for releasing the implant, and risk to the patient. With the slitter of the present invention, however, the likelihood of such "binding up" is reduced.

Further improvements in the smoothness and reliability of stent release are accomplished by providing the outer sleeve with a plurality of slits that go through the wall thickness of the outer sleeve and allow that outer sleeve to "breathe" radially in and out, as it is pulled proximally down the length of the implant bed, during release of the implant. If one supposes that the implant includes features such as radiopaque markers or membrane coatings, that can give rise to local variations of implant diameter, then an ability in the outer sleeve to "breathe" radially in and out as it slides proximally over these diameter variations, will reduce the likelihood of the binding of the proximally retreating outer sleeve on the structure radially inside it, during implant release.

Judicious design of the slits can accomplish the objective of breathability of the proximally retreating outer sleeve, without total loss of the hoop stress in the outer sleeve that will contribute to radial restraint of the radially compressed implant, prior to its release. Note, however, that the slits need not be provided in the inner sleeve and that the hoop stress in the inner sleeve, alone, can be sufficient to constrain the stent until the moment of its release. The presently preferred arrangement of through slits is to provide two or more sets of such slits, each set being a plurality of the slits, co-linear, and with each slit having a length less than 20% of the length of the implant bed, and with the slits regularly spaced from each other by a spacing that is comparable with the length of each slit, but somewhat less than the length of each slit. In the embodiment illustrated below, there are just two such sets of slits, spaced 180° apart from each other around the circumference of the implant bed, and with the slits of one set staggered along the length of the sleeve, relative to the slits of the other set. However, three or more sets of slits can be provided, where the sets of slits are similarly evenly spaced apart in the circumferential direction and staggered.

Turning to the construction of the slitter, the presently preferred device takes the form of a slitting wire that extends distally, beyond the distal end of the implant bed, but not quite as far distally as the rolling edge of the membrane prior to actuation of the stent release means. This wire lies against the luminal surface of the inner sleeve and passes through a hole in the inner sleeve, close to its distal end, then returning proximally, in the space between the inner and outer sleeves, back to a proximal end where it is secured to the device that will, at the moment of implant release, pull the outer sleeve proximally. The pulling of the wire proximally, contemporaneously with the outer sleeve, will cause the wire to slit the material of the inner sleeve, commencing at a point on the circumference of the hole that is at the proximal-most point of that circumference and progressing proximally, parallel to the longitudinal axis of the delivery system. Just as the membrane has a rolling edge, so does the slitting wire, at the point where it doubles back on itself, as it passes from inside the inner sleeve to radially outside it. This rolling edge moves along the length of the wire, as the wire "rolls" over the inner sleeve. Simultaneously with this slitting, the rolling edge of the rolling membrane is moving proximally, thereby resulting in the slit portion of the inner sleeve radially overlying the remaining unslit portion of the inner sleeve, until the full length of the implant has been released.

BRIEF DESCRIPTION OF THE DRAWINGS

FIG. 1 is a longitudinal diametral section of the distal end of a first embodiment of stent delivery catheter system;

FIG. 2 is a view of the distal end of FIG. 1, along arrow II, partly in section

FIG. 3 is a view of the distal end of a second embodiment of a stent delivery catheter system, looking into the plane of the paper; and FIG. 4 is a lateral view of what is shown in FIG. 3, from a viewpoint 90° away from the FIG. 3 viewpoint.

DETAILED DESCRIPTION

Looking first at FIG. 1 we see a self-expanding stent 10 radially confined within a rolling membrane 12 which features an inner sleeve 14, an outer sleeve 16 and a rolling edge 18 distal of the bed 20 that receives the stent 10. The bed 20 is on a shaft 22 that defines a guidewire lumen 24 and carries an atraumatic tip 26 that has a rebate 28 to receive the distal end of the rolling membrane 12 and the rolling edge 18.

At the proximal end of the inner sleeve 14, the rolling membrane 12 is secured at an annulus 30 to the shaft 22. The other end of the rolling membrane 12 extends along the shaft proximally until its end 32 is proximal of a collar 34 that is freely slidable on the abluminal surface of the shaft 22. The membrane 12 is secured to the abluminal surface of the collar 34. The collar 34 is on the distal end of a pull wire 36 that runs all the way to the proximal end of the catheter delivery system of which the distal end is shown in FIG. 1. The reader will appreciate that, when the time comes to release the stent 10, actuation is accomplished by pulling proximally on the pull wire 36, to pull the collar 34 proximally and in turn cause the rolling edge 18 of the membrane 12 to advance proximally, all the way down the length of the stent bed 20 and stent 10. A casing tube 38 defines the passing diameter of the shaft of the catheter system. Into the distal end 40 of the casing tube 38 is drawn, during release of the stent, the length of the outer sleeve 16 of the rolling membrane 12 and, after that, much of the length of the inner sleeve 14, until the rolling edge 18 has cleared the proximal end of the stent 10. Readers will appreciate that this process puts the loose material of the rolling membrane 12 snugly inside the casing tube 38 so that, when the catheter system comes to be withdrawn fully from the patient, the loose folds of the relaxed rolling membrane 12 will not be dragging along the tissue that defines the walls of the lumen in which the catheter system has been advanced.

So far, the description of the operation of the system is as in applicants prior published WO2010/076052, from which the basic elements of FIG. 1 are borrowed.

But now suppose that conditions are artificially manipulated, to make them excessively more demanding. Perhaps the rolling membrane is too thin, or the stent 10 has excessive radial force and is longer than is shown in FIG. 1. Conceivably, when pulling on the pull wire 36, some impediment then arises, to the proximal movement of the rolling edge 18, long before that edge 18 has cleared proximally the proximal end of the stent 10. Once the material of the outer sleeve 16, close to the rolling edge 18 begins to bind on the material of the inner sleeve 14, there is a possibility that material in the outer sleeve 16, proximal of the point of binding, will neck in under the higher levels of longitudinal stress in which it finds itself. Pursuing our imagination, when the whole system binds up, in this way, it might be with a long stent only partially released to the bodily lumen, with the proximal portion of the stent still captured within the catheter delivery system, and no evident way for the doctor to complete the release of the stent. Such situations are not tolerable. They can be managed by the modification and improvement now to be described.

Attention is again directed to FIG. 1. We see a portion of the shaft 22 and the bonding 30 of the proximal end of the inner sleeve 14 to the shaft 22. Again, the proximal end of the outer sleeve 16 is bonded to the collar 34 which is free to slide on the length of the shaft 22.

A slitting wire 50 is bonded, with the inner sleeve 14, to the shaft 22 at the annulus 30. It advances distally, radially inside the inner sleeve 14, as far as a hole 52 in the rolling membrane 12 (FIG. 3) proximal of, but near to, the rolling edge 18. The wire 50 doubles back on itself at that point, and returns proximally, all the way to the collar 34, between the inner 14 and outer 16 sleeves. Note how the section of FIG. 1 includes both the pull wire 36 and the slitting wire 50, meeting at the collar 34.

Note also that the slitting wire 50 is free of slack, between the hole 52 and the collar 34, so that the wire 50 begins to slit the membrane 12 at the edge of the hole 52 as soon as there has been some proximal movement of the collar 34 that imposes sufficient tension on the wire 50. The reader will recall that the self-expanding implant is imposing an outwardly directed radial force on the inner sleeve 14, putting it in tension and facilitating the task of the wire 50 to slit the membrane. The reader will also understand that, from the first proximal movement of the collar 34, longitudinal slitting of the inner sleeve 14 is occurring contemporaneously with proximal movement of the rolling edge 18 of the membrane. In this way, any hoop stress in the proximally retreating outer sleeve 16 proximal of the rolling edge 18 will gradually reduce once the rolling edge is proximal of the hole 52, as progressively more and more of the length of the outer sleeve, rolled back from the inner sleeve 14, is slit by the wire and so unable to contribute any further hoop stress. The progressive loss of hoop tension in the outer sleeve 16 reduces the likelihood of the outer sleeve 16 attracting enough frictional resistance for it to "bind up" on the abluminal surface of the inner sleeve 14 and frustrate further proximal movement of the collar 34.

The preferred slitter at the moment is the slitting wire shown in FIGS. 1 and 2. However, other slitters are contemplated. For example, the outer sleeve 16 could carry near its distal end a small cutting edge or hook that scores or slits the material of the inner sleeve 14. As the rolling edge 18 moves proximally down the length of the inner sleeve 14, so does the slitter located on the outer sleeve 16 proximal of the rolling edge 18, thereby to score or slit the inner sleeve 14, through the full length of the stent bed.

Turning to the embodiment of FIGS. 3 and 4, we see the same slitting wire 50, hole 52 and inner sleeve 14.

FIG. 3 looks at the rolling membrane from radially outside, so we see the abluminal surface of the outer sleeve 16 and the rolling edge 18. We see five short slits 60 that, in aggregate, extend over the full length of the stent bed 20. The slits are shown all the same length but optimization of design might lead to a solution in which the slits are different lengths. Likewise, the gap 66 between each of the co-linear slits 60 of the line of slits might be a different length of gap between any two slits but, in the simple situation shown in FIG. 3, each of the gaps is the same length, about one third of the length of each slit.

In the FIG. 4 view, 90° around the circumference from the view of FIG. 3, we see a second set of co-linear slits 62 with gaps 64 in between them. One should note that the slits 62 are longitudinally staggered relative to the slits 60 of FIG. 5 so that in any transverse section that includes a gap 64, there is present a slit 60. In any transverse section that includes a slit 62, there is a gap 66 between the slits 60 above and below the plane of the section on the other side of the circumference of the sleeve 16.

The reader is invited to contemplate the situation that the implant inside the rolling membrane shown in FIGS. 3 and 4 has at points spaced from both its ends one or more zones of somewhat greater outside diameter than the nominal diameter. Such rings of marginally greater diameter can be a source of friction and possibly resistance to further proximal sliding movement of the outer sleeve 16. However, the presence of the slits 60, 62, would allow a degree of diametral expansion not available without the slits 60 and 62, for the outer sleeve 16 to ease outwardly as it slides over the zone of greater diameter within its lumen. The phenomenon has been recognized by the present inventors and has been named "breathing". With the slits, the outer sleeve can "breathe" as required, as it proceeds proximally during release of the stent.

Staggering of the sets of slits as described earlier can reduce or eliminate any longitudinal portions of the sleeve along the length of the stent bed that are not slit at some point along their circumference. This advantageously contributes to the "breathing" effect.

Summarizing, taking the rolling membrane concept of FIG. 1, and applying it to ever-longer self-expanding stents of ever-greater radial force and ever-greater component complexity will place ever-increasing demands on the delivery systems designer to ensure that there is no binding up of the rolling membrane during progressive release of the implant. The simple system of FIG. 1 can be rendered more tolerant of variations of diameter of the implant within the membrane, and of unpredictability of materials performance in the material of the membrane itself, by including a slitter in accordance with the present invention. Endowing the outer sleeve with a "breathing" capability will further enhance the performance of the system and allow its application to ever-longer stents of a greater structural complexity and performance capability.

This detailed description concentrates on the components of the inventive concept. Readers will well understand that all sorts of variations and modifications are open to them. Readers who are experienced in the design of delivery systems for self-expanding implants will have their own suite of design expertise and capabilities. They will know how to take the inventive concept of the present invention and utilize it within the constraints of their own system architectures.

Further, experienced readers are knowledgeable in choice of materials for implant delivery systems, and in the design judgments that are routinely made when putting together the elements of a function system that will deliver performance enhancements.

What is claimed is:

1. A delivery device for a self-expanding implant, comprising:
   an inner shaft;
   a collar disposed over the inner shaft;
   an actuation member coupled to the collar;
   a rolling membrane disposed over the self-expanding implant, the rolling member including a proximal end secured to the inner shaft, and a distal end secured to the collar; and
   a slitting member, including a proximal end secured to the inner shaft, and a distal end secured to the collar, wherein translation of the collar over the inner shaft in a proximal direction contemporaneously translates the rolling membrane and the slitting member in the proximal direction.

2. The delivery device according to claim 1, wherein the rolling membrane comprises an outer sleeve and an inner sleeve, wherein the outer sleeve includes a plurality of slits.

3. The delivery device according to claim 2, wherein each of the plurality of slits have a length which is less than 20% of a length of the self-expanding implant.

4. The delivery device according to claim 2, wherein a first set of the plurality of slits is arranged co-linear along a length of the rolling membrane, and wherein a second set of the plurality of slits is arranged co-linear to the first set of the plurality of slits and evenly spaced therefrom.

5. The delivery device according to claim 2, wherein the slitting member comprises a wire that extends distally from the proximal end of the slitting member to a distal end of the self-expanding implant, passes through the inner sleeve, and extends proximally between the inner sleeve and the outer sleeve to a point proximal of the self-expanding implant.

6. The delivery device according to claim 1, wherein the slitting member is arranged to commence at a point that is at or near a distal end of the self-expanding implant.

7. The delivery device according to claim 1, wherein the actuation member is a pull wire.

8. The delivery device according to claim 1, wherein the inner shaft defines a guidewire lumen.

9. The implant delivery device according to claim 1, wherein the rolling membrane comprises a cold-drawn polyethylene terephthalate material.

10. A method of releasing a self-expanding implant in a patient, comprising:
    introducing the self-expanding implant to a target location via a delivery system, the delivery system comprising:
      an inner shaft;
      a collar disposed over the inner shaft;
      an actuation member coupled to the collar;
      a rolling membrane disposed over the self-expanding implant, the rolling member including a proximal end secured to the inner shaft, and a distal end secured to the collar; and
      a slitting member, including a proximal end secured to the inner shaft, and a distal end secured to the collar;
    actuating the actuation member to translate the collar over the inner shaft away from the self-expanding implant, thereby contemporaneously translating the rolling membrane and the slitting member away from the self-expanding implant.

* * * * *